United States Patent [19]

Jackson et al.

[11] Patent Number: 4,663,127

[45] Date of Patent: May 5, 1987

[54] GAS FLOW CARTRIDGE HAVING RESILIENT FLEXIBLE MEMBRANE WITH SLIT SEPARATING REACTION AND REAGENT CHAMBERS

[75] Inventors: Jacqueline J. Jackson; Anatoly Dvornichenko, both of Denver; Daniel Cooper, Parker, all of Colo.

[73] Assignee: Hemotec, Inc., Denver, Colo.

[21] Appl. No.: 434,569

[22] Filed: Oct. 15, 1982

[51] Int. Cl.[4] ............................................. G01N 33/86
[52] U.S. Cl. ....................................... 422/58; 73/64.1; 356/39; 422/61; 422/73; 422/103; 436/69; 436/165
[58] Field of Search ............... 422/100, 101, 102, 103, 422/73, 57, 58, 61, 119, 44, 47; 436/69, 165, 809; 356/39; 73/64.1, 57; 435/13; 210/918

[56] References Cited

U.S. PATENT DOCUMENTS

| | | |
|---|---|---|
| 2,129,043 | 9/1938 | Bortsch . |
| 3,038,327 | 6/1962 | Resnick . |
| 3,077,106 | 2/1963 | Fink . |
| 3,307,392 | 3/1967 | Owen et al. . |
| 3,450,501 | 6/1969 | Oberhardt . |
| 3,492,096 | 1/1970 | Hattersley . |
| 3,525,254 | 8/1970 | Milanes . |
| 3,560,162 | 2/1971 | Mittleman . |
| 3,560,163 | 2/1971 | Mittleman . |
| 3,635,678 | 1/1972 | Seitz et al. . |
| 3,658,480 | 4/1972 | Kane et al. . |
| 3,692,487 | 9/1972 | Sanz . |
| 3,695,842 | 10/1972 | Mintz . |
| 3,704,099 | 11/1972 | Sanz . |
| 3,713,780 | 1/1973 | Shapiro . |
| 3,715,189 | 2/1973 | Nighohossian et al. ............... 422/61 |
| 3,719,075 | 3/1973 | Mandrona et al. . |
| 3,741,002 | 6/1973 | Simons . |
| 3,814,585 | 6/1974 | Bailly . |
| 3,854,324 | 12/1974 | Altshuler et al. . |
| 3,911,728 | 10/1975 | Fixot . |
| 3,918,908 | 11/1975 | Moyer et al. . |
| 3,963,349 | 6/1976 | Albright et al. . |
| 4,000,972 | 1/1977 | Braun et al. ............... 436/69 |
| 4,074,971 | 2/1978 | Braun et al. ............... 436/69 |
| 4,081,242 | 3/1978 | Girolami . |
| 4,182,739 | 1/1980 | Curtis ............... 422/47 |
| 4,197,735 | 4/1980 | Munzer et al. ............... 422/100 |
| 4,210,623 | 7/1980 | Breno et al. ............... 422/101 |
| 4,371,498 | 2/1983 | Scordato et al. . |

Primary Examiner—Arnold Turk
Attorney, Agent, or Firm—John R. Ley

[57] ABSTRACT

A gas flow cartridge in which to conduct analytical coagulation tests on a sample of fluid such as blood includes a tube-like member and a resilient flexible membrane having a slit formed therethrough to divide the tube-like member into an upper reaction chamber in which the test takes place and into a lower reagent chamber which initially contains reagent to be mixed with the sample of liquid upon which the test is to be conducted. The contents of the reagent chamber are forced through the slit in the resilient flexible membrane due to the flexing of the membrane around the slit when pressure is applied. Once the reagent is in the reaction chamber with the sample of fluid, a flow of gas is forced upward through the slit in the membrane during the analytical test.

6 Claims, 2 Drawing Figures

GAS FLOW CARTRIDGE HAVING RESILIENT FLEXIBLE MEMBRANE WITH SLIT SEPARATING REACTION AND REAGENT CHAMBERS

This invention pertains to detecting coagulation and coagulation-related factors in fluids, particularly blood. More particularly, the present invention pertains to an improvement in a gas flow cartridge within which analytical coagulation tests are conducted. The improvements claimed herein are also disclosed in a United States patent application for Coagulation Detection by Gas Flow or Plunger Sensing Techniques, Ser. No. 434,718, now U.S. Pat. No. 4,599,219, filed concurrently herewith and assigned to the assignee of the present invention.

Prior U.S. Pat. Nos. 4,074,971 for Apparatus and Method for the Pharmacological Manipulation of Coagulation Mechanism in Blood and for Signalling the Event of Blood Coagulation, and 4,000,972 for Measuring System for the Pharmacological Manipulation of the Coagulation Mechanism in Blood and for the Elapsed Coagulation Time, both of which are assigned to the assignee of the present invention, disclose gas flow cartridges wherein gas is bubbled upwardly through a pool of liquid or blood upon which the coagulation test is conducted. The pool of liquid is contained within a reaction chamber defined by a tube-like member of the cartridge. A partitioning arrangement formed of the same material as the tube-like structure separates the reaction chamber from a reagent chamber which is positioned below the reaction chamber in the tube-like member. The reagent chamber contains a reagent or substance which is mixed with the liquid in the reaction chamber at the commencement of the test. The lower end of the reaction chamber is sealed by a movable lower plug member extending across and sealing against the lower bottom opening of the tube-like member. At the commencement of the analytical test, the lower plug member is moved upward, and a portion of the partition is broken away, as disclosed in the aforementioned two U.S. patents, and the contents of the reagent chamber are forced into the liquid in the reaction chamber.

The reagent chamber is filled with the reagent at the time of manufacturing the cartridge. A considerable amount of time may lapse between manufacture of the cartridge and its use. The cartridge will be transported from the manufacturer to the user and may be subjected to rough handling. The storage conditions may not be or remain favorable. The quantity and quality of the reagent in the reagent chamber is critical to obtain reliable test results. It is therefore important to maintain the exact quantity of reagent in the reagent chamber over long periods of time and under different handling and storage conditions.

Use of the integral break-away portion of the partition, as disclosed in the aforementioned two U.S. patents, has the advantage of integrally sealing the reaction and reagent chambers prior to use of the cartridge. However, some relatively precision manufacturing techniques are required to form the relatively small and delicate break-out portion of the partition. The application of force is required to break out the break-away portion of the partition, and there is some possibility that the force could also fracture or break other portions of the cartridge, and thereby ruin it for use in the particular test or adversely influence the test results. The broken out portion is loose in the reaction chamber and may move about and provide a false indication of coagulation by influencing an optical sensing arrangement employed to detect coagulation.

INVENTION SUMMARY

The improved gas flow cartridge of the present invention includes a means including a resilient flexible membrane within the tube-like member of the cartridge to initially separate and seal the reagent chamber from the reaction chamber. The membrane has at least one slit formed through it. The resiliency of the material normally closes the slit and seals the chambers against fluid communication therebetween. Upon a predetermined increase in pressure, the portion of the membrane adjacent the slit resiliently flexes to open the slit. The increase in pressure results when a lower plug member at the lower end of the reagent chamber is pushed upward. As the lower plug member moves upward, the contents of the reagent chamber pass through the open slit in the membrane and into the liquid in the reaction chamber. The membrane is preferably a part of an upper plug member which has a similar configuration to the lower plug member and which is inserted into the tube-like member during assembly of the cartridge. The upper plug member can be separately formed from the tube-like member to simplify the construction and formation of the tube-like members. The resiliency of the upper plug member maintains the seals at the slit and at the side walls of the tube-like member over long periods of time and under different conditions. The flexibility of the membrane eliminates the possibility of pressure forces cracking the tube-like member. No broken away or loose parts which might influence a detection of coagulation are present in the reaction chamber. After the termination of gas flow therethrough at the end of the analytical test, the portion of the membrane adjacent the slit flexes back to its normal position and the slit closes to seal the contents within the reaction chamber and prevent leaking.

The nature and details of the present invention can be more completely understood by reference to the following description of the preferred embodiment taken in conjunction with the drawings, and from the appended claims.

DRAWING DESCRIPTION

DETAILED DESCRIPTION

Figures 1, 2:
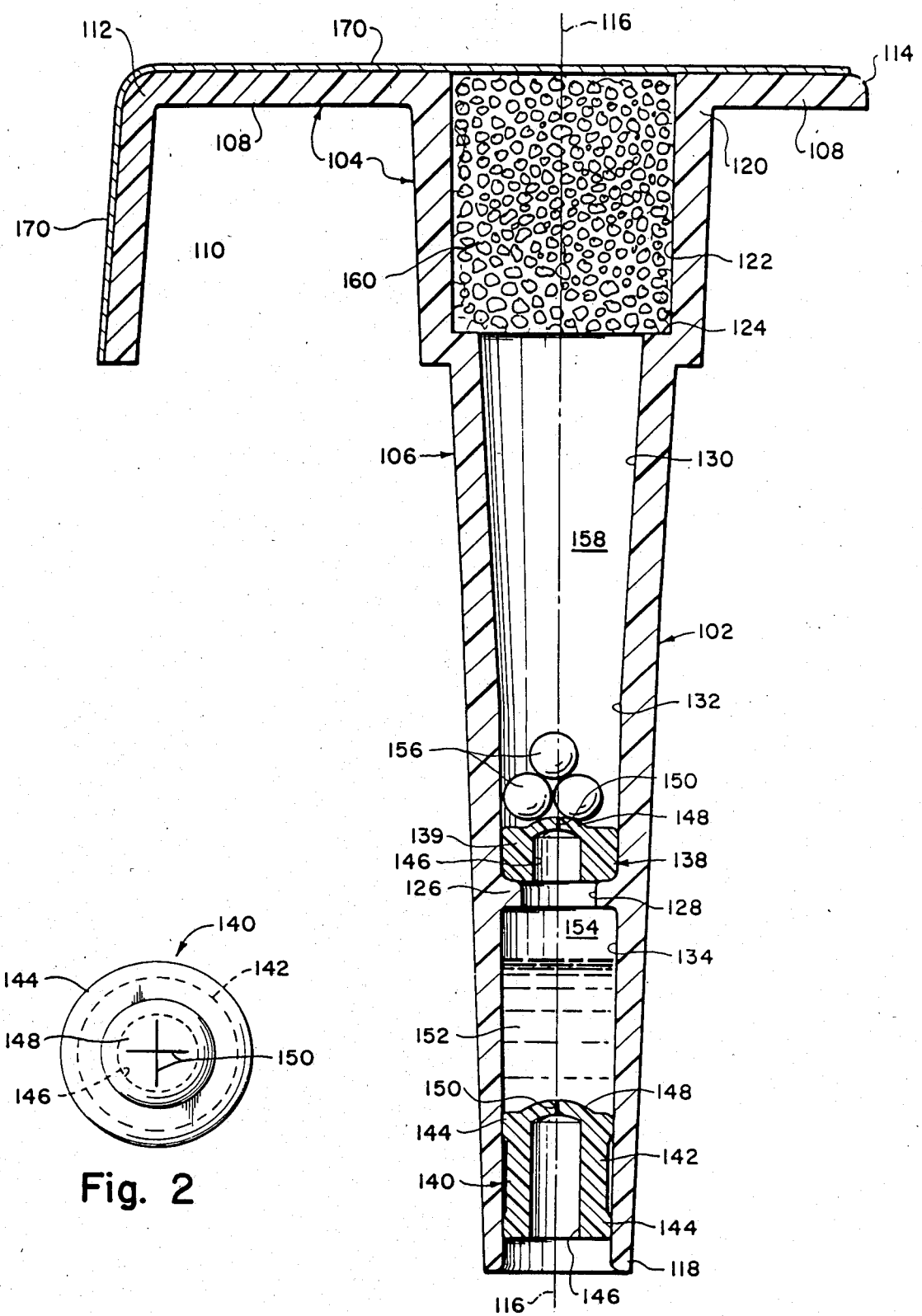
FIG. 1 is a vertical section view taken through the axis of one of the tube-like members of the improved gas flow cartridge of the present invention.
FIG. 2 is a top plan view of a plug member shown in FIG. 1.

In general, analytical tests utilizing the improved gas flow cartridge 100 shown in FIG. 1 proceed by directing a flow of gas upward through each of a plurality of test cells of the cartridge such as the one illustrated at 102. The interaction of the gas with the sample of fluid in the test cell create conditions which allow a machine to detect and measure coagulation and coagulation-related factors. The details of the machine with which the cartridge 100 is utilized to conduct the analytical tests are disclosed in the aforementioned U.S. patent application for "Coagulation Detection by Gas Flow or Plunger Sensing Techniques", Ser. No. 434,718, filed concurrently herewith. The specification of this application is incorporated herein by this reference.

The gas flow cartridge includes a housing 104 preferably formed of integral clear acrylic plastic. Four transversely aligned and vertically open tube-like members 106 extend downward from an upper shelf portion 108 of the housing 104. A lip 110 extends downward from a forward edge 112 of the shelf portion 108. The tube-like members 106 are positioned intermediate the front edge 112 and a rear edge 114 of the shelf portion 108, and are spaced in transverse alignment at equal intervals along the shelf portion 108. Each of the tube-like members 106 has essentially the same predetermined configuration, and its shape is concentric about a center axis 116 through each tube-like member 106.

The tube-like member 106 defines the enclosure of each test cell 102. Each tube-like member 106 has an open lower end 118 and an open upper end 120. The upper end 120 is integrally connected to the shelf portion 108. An initial upper portion of the tube-like member extends downwardly from the upper end 120 and defines an interior, generally cylindrical surface 122. The extent along the axis 116 to which the cylindrical surface 122 extends is approximately the same as that distance which the lip 110 extends downward from the forward edge 114 of the upper shelf portion 108. An annular shoulder 124 extends radially inward at the lower end of the cylindrical surface 122. A partition 126 extends radially inward toward the axis 116 from each tube-like member 106 at a position intermediate the shoulder 124 and the lower end 118. A cylindrical axial passageway 128 extends axially through the partition 126. A downwardly-converging, frustoconical-shaped inner surface 130 extends from the shoulder 124 to a position intermediate the shoulder 124 and the partition 126. A substantially cylindrical surface 132 extends from the lower end of the frustoconical-shaped surface 130 to the partition 126. Another cylindrical surface 134 extends downward from the partition 126. The lower edge of the cylindrical surface 134 is divergently curved radially outward at the lower end 118 of the tube-like member.

An upper plug member 138 and a lower plug member 140, each of which is formed of resilient, flexible material such as Kraton, are frictionally received within the interior opening of the tube member 106 defined by the surfaces 132 and 134, respectively. Both plug members 138 and 140 have rotational concentricity about the axis 116. The upper plug member 138 includes a generally cylindrical main body portion 139. The lower plug member 140 includes a generally cylindrical main body portion 142 from which a pair of ring-like edges 144 protrude outwardly at each axial end of the plug member 140, as is also shown in FIG. 4. A center cylindrical opening 146 extends axially through both main body portions 139 and 142. An upwardly convex-shaped dome portion 148 of uniform thickness extends across the upper axial end of each main body portion 139 and 142 and closes the center opening 146 at its upper end. A pair of crossing diametrical slits 150 extends completely axially through the dome portion 148 at the axis 116 of each plug member. The slits preferably cross one another at right angles. The terminal ends of the slits 150 are slightly radially inwardly spaced from the inner surface of the center opening 146. A coating of a lubricant-like sealant may be applied to the slits 150. The sealant further assures closure of the slits prior to use. The sealant should be non-hydroscopic, have relatively low shear strength to allow the slits 150 to open, have the ability to adhere to the dome portion, and be compliant to move slightly with the dome portion prior to use of the cartridge.

The upper plug member 138 is inserted from the upper end 120 of the tube-like member 106 downwardly along the surface 134 until the lower end of the main body portion 139 contacts and rests on the partition 126. The center opening 146 of the plug member 138 extends upward from the passageway 128 in the partition 126, and the dome portion 148 is spaced above the partition 126 by the axial length of the center opening 146. The cylindrical exterior side walls of the main body portion 139 contact, frictionally engage and seal with the surface 132 of the tube-like member. The main body portion is slightly radially compressed when in contact with the surface 132 to develop sufficient retention force to hold the upper plug member 138 in place during use of the cartridge.

The plug member 140 is inserted from the lower end 118 of the tube-like member 106 upwardly along the surface 134. The edges 144 frictionally engage with, and resiliently seal against, the surface 134 of the tube-like member. The resiliency of the material of the dome portion 148 of both plug members 138 and 140 normally holds the slits 150 in a closed sealed position, thereby preventing the passage of fluid through the slits 150.

The upper plug member 138 is first inserted into the tube-like member 106. Before the lower plug member 140 is inserted into the lower end of the lower center opening 134, a predetermined quantity and type of reagent 152 is inserted into a reagent chamber 154. The reagent chamber 154 is enclosed and defined at the upper end by the upper plug member 138, at the sides by the surface 134, and at the lower end by the lower plug member 140 which is resiliently sealed against the interior surface 134 of the tube-like member. The slits 150 remain closed to confine the reagent 152 to the reagent chamber 154. To insert the reagent 152 into the reagent chamber 154, the housing 104 is inverted from the position shown in FIGS. 2 and 3, and the reagent 152 is added into the reagent chamber. A wire is placed alongside the lower plug member 140 as it is inserted into the lower open end of the tube-like member, and then the wire is removed. The wire deforms the edges 144 to vent air from the reagent chamber as the lower plug member moves into the reagent chamber.

The type and quantity of reagent 152 inserted into the reagent chamber 154 depends on the purpose for which the cartridge 100 is to be used. For dose response tests, heparin will typically be part of the reagent. A different quantity of heparin will be introduced into the reagent chambers of each of the test cells 102 in a single cartridge 100. For titration tests, the reagent could include heparin or protamine, in variable amounts in the reagent chambers of the test cells of the cartridge. For clotting time tests, the same predetermined quantity of activating substance is introduced into each of the reagent chambers in each of the test cells 102.

At least one and preferably three small ball members 156 are inserted into a reaction chamber 158 of the tube-like member 106. The reaction chamber 158 is defined on the sides by the surfaces 130 and 132 and extends axially above the upper plug member 138 to the shoulder 124. The balls 156 are preferably formed of glass. The glass surfaces of the balls 158 react beneficially with the blood, in a manner thought to simulate the glass test tubes and containers in which laboratory tests are typically carried out. For determining coagulation and coagulation-related factors in other types of fluid, the balls may be dispensed with, or they may be constructed from other types of material.

An open-cell foam member 160 is inserted from the upper end 120 into the upper interior opening in the tube-like member 106 defined by the cylindrical surface 122. The foam member 160 is preferably of a right cylindrical configuration, and its axial length is approximately the same as the length between the shoulder 124 and the upper end 120 of the tube-like member 106. The foam member 160 is inserted downwardly until it contacts the shoulder 124, and the lower edge of the foam member extends across the upper margin of the reaction chamber 158. Prior to insertion in the tube-like member, the foam member 160 and its internal structure is coated with a debubbling agent such as silicone. The debubbling agent causes liquid contacting the strand-like or fiber-like internal structure of the foam material 160 to reflux or drain downward and not collect in the interstices in the foam material. Preferably, the foam material is formed of synthetic plastic.

A cover 170 is attached to the upper surface of the shelf portion 108. The cover preferably also extends around and down on the front outer surface of the lip 110. The cover 170 is preferably a single piece of paper and is attached preferably by gluing it around the outer edges of the shelf portion 108, and on the outer front surface of the lip 110. The paper cover 170 contains printed indicia indicative of the type of analytical test to be conducted with the cartridge. The type of test is determined by the type and quantity of reagent 152 present in the reagent chamber 154. Furthermore, printed indicia may also indicate the quantities or strengths of reagent in the reagent chambers.

Prior to using the flow cartridge in an analytical test conducting machine, a predetermined quantity of blood or other fluid is inserted into each reaction chamber 158. Typically, the blood is injected from a syringe by piercing the paper cover 170 with the syringe needle and extending the needle through the foam material 160. The injected blood collects at the bottom of the reaction chamber 158 above the upper plug member 138. After the cartridge 100 is inserted into an analytical test conducting machine, the machine operatively forces the plug member 140 upward until its dome portion 148 contacts the lower edge of the partition 126. As the plug member 140 is forced upward, the slit 150 of the upper plug member 138 is forced open by pressure in the reagent chamber 152 and the reagent in the reagent chamber is forced upwardly through the passageway 128 of the partition 126 and through the open slit 150 of the upper plug member 138 and into the reaction chamber 158. The reagent 152 mixes with the blood collected in the bottom of the reaction chamber 158. Thereafter, a stream of pressurized gas is forced through the center opening 146 of the plug member 140. The pressurized gas opens the slits 150 of both plug members 138 and 140 and passes therethrough. The gas agitates the balls 156 and causes mixing of the reagent and the blood in the reagent chamber 158 and also causes bubbles of blood to be formed above the surface of the pool in the reaction chamber. The bubbles are transported upwardly by the flow of gas and contact the lower surface of the foam member 160. So long as the blood of the bubbles remains liquid, i.e., does not clot or coagulate, the liquid blood does not collect in the interstices of the foam material 160, due to the effect of the debubbling agent. When coagulation commences, the liquid blood turns to a solid or to a state of substantially higher viscosity and begins to collect in and inundate the interstices of the foam material 160, and the debubbling agent is ineffective or substantially less effective. The collection of the coagulated blood in the foam material 160 is optically sensed to detect the event of coagulation. During this operation, gas escapes out of the top of each tube-like member through the hole formed in the upper cover member 170 by the syringe needle which inserted the blood or other fluid into the reaction chamber 158.

In some circumstances, the upper plug member 138 may have substantially the same configuration as the lower plug member 140. The plurality of slits 150 in the plug members reduces the pressure required to force bubbles through the slits of both plug members. Use of the upper plug member 248 may eliminate the need for manufacturing the partition 126, or a partition with a break-out portion, as a part of the tube-like member 106.

The resilient, flexible and sealing characteristics of the material of the upper and lower plug members effectively seal the reagent in the reagent chamber. The inherent resiliency of the plug member material maintains the integrity of the seals over relatively long periods of time. Reagent does not leak out of the reagent chamber, and atmospheric gasses are not admitted to the reaction chamber. Rough handling prior to use does not fracture or dislodge the flexible plug members, as might occur with rigid structures or those rigidly sealed to the tube-like member. Manufacturing the cartridge may be simplified since the plug members can be formed separate and apart from the tube-like members. The flexibility of the material of the plug members avoid creating detrimental forces that might crack or fracture portions of the tube-like member, as is a possibility in prior cartridges with break-out portions. No loose parts or broken away portions are produced which might move about the reaction chamber during the test and cause a false indication of coagulation. After the analytical test and the gas flow has terminated, the slits in both the upper plug member and lower plug member return to the closed sealed position and provide two seals to prevent the contents of the reaction chamber from leaking out after the test.

The nature and operation of the present invention has been shown and described with a degree of specificity. It should be understood, however, that the specificity of the description has been made by way of preferred example and that the invention is defined by the scope of the appended claims.

What is claimed is:

1. A cartridge in which to conduct an analytical test on fluid material inserted therein, the analytical test including the step of flowing pressurized gas into the cartridge to operatively interact the gas with the fluid material during the course of the analytical test, said cartridge comprising:

a tube-like member having an open interior extending generally axially therethrough from a lower end to an upper end;

dividing means within the open interior of the tube-like member at a position intermediate the upper and lower ends for dividing the tube-like member into a reagent chamber between said dividing means and the lower end and into a reaction chamber between said dividing means and the upper end, the reaction chamber adapted to receive and hold an inserted fluid material for interaction with gas during an analytical test;

a passageway defined by said dividing means and extending between the reagent and reaction chambers;

plug means operatively sealing the open interior of the reagent chamber at a position initially spaced from the dividing means and adjoining the lower end of the tube-like member, said plug means adapted for operative movement toward the dividing means to reduce the volume of the reagent chamber, said plug means further including means for admitting and conducting pressurized gas into the cartridge during the analytical test;

a quantity of fluid reagent initially confined within the reagent chamber; and means for opening and closing the passageway in response to fluid pressure within the reagent chamber, said opening and closing means operatively (a) normally maintaining the passageway sealed to prevent the reagent from flowing into the reaction chamber prior to commencement of the analytical test, (b) opening the passageway in response to an increase in fluid pressure within the reagent chamber upon the upward movement of the plug means toward the dividing means, (c) maintaining the passageway open to conduct the fluid reagent therethrough into the reaction chamber as the plug means moves upward toward the dividing means, (d) opening the passageway in response to the presence of pressurized gas admitted at the plug means (e) maintaining the passageway open to conduct the admitted pressurized gas into the reagent chamber during the analytical test, and (f) sealing the passageway in response to the termination of the supply of pressurized gas at the conclusion of the analytical test to prevent the material in the reaction chamber from leaking through the passageway at the conclusion of the analytical test.

2. A cartridge as defined in claim 1 wherein said fluid pressure responsive means for opening and closing the passageway comprises a resilient flexible member having resilient characteristics which normally opens the passageway when relative pressure differential between the regent chamber and the reaction chamber exceeds a predetermined amount, and which flexes under the predetermined amount of pressure differential to open the passageway to the flow of fluid therethrough.

3. The cartridge as defined in claim 2 wherein the flexible member includes a normally closed opening which opens under the predetermined amount of pressure differential.

4. The cartridge as defined in claim 3 wherein the normally closed opening comprises a slit formed through the resilient flexible member.

5. A cartridge as defined in claim 3 wherein the resilient flexible member includes a slit formed therethrough, and the resiliency of the flexible member normally holds the slit in a closed position to seal the slit against the passage of fluid therethrough, and a portion of the member adjacent the slit resiliently flexes under the influence of the predetermined fluid pressure to open the slit and allow fluid communication therethrough.

6. A cartridge as defined in claim 5 wherein said plug means further comprises a dome portion formed of resilient flexible material, and said means for admitting and conducting pressurized gas into the cartridge includes a slit formed through the dome material.

* * * * *